(12) United States Patent
Kunisada

(10) Patent No.: US 9,186,226 B2
(45) Date of Patent: Nov. 17, 2015

(54) CONTROL DEVICE OF DENTAL HANDPIECE

(75) Inventor: Makoto Kunisada, Kanuma (JP)

(73) Assignee: HAKANISHI INC., Tochigi (JP)

( * ) Notice: Subject to any disclaimer, the term of this patent is extended or adjusted under 35 U.S.C. 154(b) by 153 days.

(21) Appl. No.: 14/119,993

(22) PCT Filed: May 23, 2012

(86) PCT No.: PCT/JP2012/003370
§ 371 (c)(1),
(2), (4) Date: Dec. 9, 2013

(87) PCT Pub. No.: WO2012/164875
PCT Pub. Date: Dec. 6, 2012

(65) Prior Publication Data
US 2014/0134565 A1    May 15, 2014

(30) Foreign Application Priority Data
May 27, 2011   (JP) .................. 2011-119079

(51) Int. Cl.
| A61C 19/04 | (2006.01) |
| A61C 1/00 | (2006.01) |
| A61C 3/02 | (2006.01) |
| A61C 1/06 | (2006.01) |
| A61C 1/12 | (2006.01) |

(52) U.S. Cl.
CPC .............. *A61C 1/003* (2013.01); *A61C 1/0007* (2013.01); *A61C 1/0015* (2013.01); *A61C 1/06* (2013.01); *A61C 3/02* (2013.01); *A61C 19/04* (2013.01); *A61C 1/12* (2013.01)

(58) Field of Classification Search
CPC ...... A61C 1/0015; A61C 1/003; A61C 1/186; A61C 5/02; A61C 5/023
See application file for complete search history.

(56) References Cited

U.S. PATENT DOCUMENTS

| 5,980,248 | A | * | 11/1999 | Kusakabe et al. | 433/27 |
| 6,616,446 | B1 | * | 9/2003 | Schmid | 433/27 |
| 6,929,476 | B2 | * | 8/2005 | Katsuda et al. | 433/98 |

(Continued)

FOREIGN PATENT DOCUMENTS

| DE | 19628854 A1 | 1/1997 |
| JP | 63-33865 B2 | 2/1988 |

(Continued)

OTHER PUBLICATIONS

International Search Report for application No. PCT/JP2012/003370 dated Aug. 21, 2012.

(Continued)

*Primary Examiner* — Ralph Lewis
(74) *Attorney, Agent, or Firm* — Pearne & Gordon LLP

(57) ABSTRACT

An object is to provide a control device of a dental handpiece that is able to prevent giving a shock to the operator having the dental handpiece and the patient of treatment subject and also that is able to reduce the load onto the motor and to suppress heat generation thereof. The rotational direction of a motor 20 of a dental handpiece is switched at every certain time. At this time, before the rotational direction of the motor 20 is switched through switching of a relay 17, voltage to be applied to the motor 20 is reduced. It is thereby prevented that a large current flows into the motor 20 when the relay 17 is switched, and also that a large rotation torque is applied to a cutting tool rotationally driven by the motor 20.

13 Claims, 15 Drawing Sheets

(56) References Cited

U.S. PATENT DOCUMENTS

| | | | |
|---|---|---|---|
| 7,901,210 B2* | 3/2011 | Heraud | 433/224 |
| 8,714,978 B2* | 5/2014 | Borgschulte | 433/224 |
| 9,017,076 B2* | 4/2015 | Danger | 433/224 |
| 2009/0136896 A1* | 5/2009 | Meyer Shuster | 433/102 |
| 2012/0301840 A1* | 11/2012 | Poli | 433/27 |
| 2013/0234627 A1* | 9/2013 | Brown et al. | 318/3 |
| 2014/0134565 A1* | 5/2014 | Kunisada | 433/27 |
| 2014/0322669 A1* | 10/2014 | Kunisada | 433/102 |
| 2015/0086937 A1* | 3/2015 | Katsuda et al. | 433/27 |
| 2015/0086941 A1* | 3/2015 | Katsuda et al. | 433/102 |

FOREIGN PATENT DOCUMENTS

| | | |
|---|---|---|
| JP | 9-38108 A | 2/1997 |
| JP | 2002-345845 A | 12/2002 |
| JP | 2003-504113 A | 2/2003 |
| JP | 2007-229110 A | 9/2007 |
| WO | 2007085966 A2 | 8/2007 |

OTHER PUBLICATIONS

Extended European Search Report for Application No. 12792892.7 dated Dec. 12, 2014.

* cited by examiner

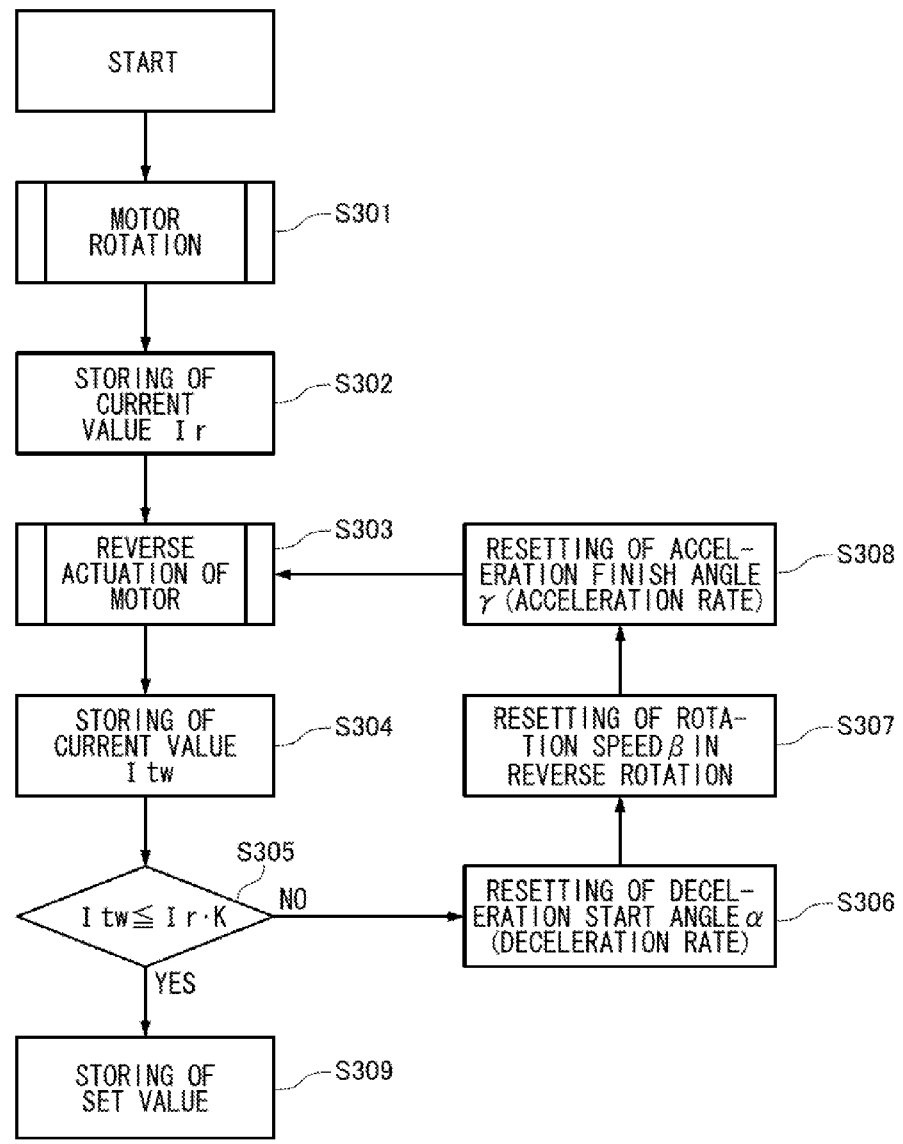

CONTROL DEVICE OF DENTAL HANDPIECE

TECHNICAL FIELD

The present invention relates to a control device of a dental handpiece for cutting a root canal(s) of a tooth (teeth).

BACKGROUND ART

A dental handpiece for cutting a root canal(s) of a tooth (teeth) is constructed so as to rotate a cutting tool using a motor.

Here, the cutting tool for cutting a root canal of a tooth has a slender configuration. At the occasion of cutting the root canal of a tooth, if the cutting tool is jammed into the root canal of the tooth, the cutting tool undergoes a force in a twisting direction, which results in a problem that the cutting tool becomes apt to be broken.

Hence, there is proposed a method that prevents a cutting tool from being jammed into a tooth (teeth) and from being damaged by causing the cutting tool to work at a forward-reverse rotation mode in which it is rotated in one direction for a certain time and thereafter is rotated in opposite direction (hereinafter, occasionally simply called as "forward-reverse rotation") (refer to, for example, Patent Document1).

In a conventional method of implementing forward-reverse rotation, as shown in FIG. 14, a voltage is applied to a motor (step S101), and the voltage is increased until the rotation speed of the motor reaches a set speed (steps S102, S103). After the rotation speed of the motor has reached the set speed, a relay is switched and the application direction of the voltage is switched at every lapse of a certain time (steps S104 to S107). The motor is thereby reversely rotated at every certain time, and the forward-reverse rotation of the cutting tool is implemented.

CITATION LIST

Patent Document

Patent Document 1: Japanese Translation of PCT International Application, Publication No. JP 2003-504113

SUMMARY OF THE INVENTION

Problems to be Solved by the Invention

However, during operation as described above, the voltage applied to the motor is rendered to be constant, and the polarity of the voltage applied to the motor is to be switched by causing a relay to be activated at every certain time, as shown in FIG. 15. Thereupon, at immediately after the relay is switched, the current applied to the motor becomes instantaneously large (hereinafter, this is called as "inrush current"). Then, a large rotation torque is applied to the cutting tool, which results in a problem that a shock is given to the operator conducting the treatment using a handpiece and the patient of treatment subject. In addition, since becoming a load onto the motor, there also is a problem that the motor generates heat.

The present invention has been accomplished in view of such the technical problems and has an object of providing a control device of a dental handpiece that is able to prevent giving a shock to the operator having the dental handpiece and the patient of treatment subject and also that is able to reduce the load onto the motor and to suppress the heat generation.

Solution to the Problems

Under such the object, a control device of a dental handpiece of the present invention includes a voltage application portion, which applies a voltage to a motor for rotating a cutting tool mounted to the dental handpiece, the motor being built in the dental handpiece; a rotational direction switching portion, which switches the rotational direction of the motor by switching a polarity of the voltage applied to the motor with the voltage application portion; and a control portion, which controls a magnitude of the voltage applied with the voltage application portion, wherein the control portion obliquely decreases the voltage to be applied from the voltage application portion to the motor (hereinafter, "the voltage to be applied from the voltage application portion to the motor" is occasionally called as "motor application voltage") in advance of switching the voltage polarity conducted by the rotational direction switching portion.

Like this, if the motor application voltage is obliquely decreased in advance of switching of the voltage polarity conducted by the rotational direction switching portion, and then the polarity of the motor application voltage is switched at the rotational direction switching portion, a low voltage is applied to the motor. The rotation speed of the motor at the time immediately after the switching is suppressed.

In order to make this effect more prominent, it is favorable to obliquely increase the motor application voltage after the switching of the voltage polarity described above.

Here, the control portion may control so that the rotational direction switching portion conducts the switching of the voltage polarity described above at every lapse of a predetermined certain time.

Moreover, the control device of a dental handpiece of the present invention may further comprise a sensor for detecting the rotation angle of the motor. In this case, the control portion may control also so that the rotational direction switching portion conducts the switching of the voltage polarity described above when the rotation angle of the motor detected by the sensor reaches a predetermined certain angle.

Incidentally, the motors operated by a control device each have an individual difference, and the individual difference varies depending on the period of usage of the control device or the motor. It is therefore favorable that, for the sake of setting an appropriate rate at which the voltage is decreased or increased, the control portion of the present invention has a function for calibrating the rate (hereinafter, called as "rate RT") at which the voltage applied from the voltage application portion to the motor is decreased or increased.

It is favorable that the control portion according to the present invention causes the rate RT to be subjected to variable control. Performing variable control of the rate RT like this gives various advantages to the present invention as explained in embodiments described later in detail.

This variable control includes at least following pattern a to pattern d.

Pattern a: The rate RT is subjected to variable control depending on the rotation speed of a motor.

The pattern a is effective to cause the rotation speed to be rendered to be variable in the case of a steady state period in which no load is applied to the motor or, even if a load is applied thereto, the load is infinitesimal. Incidentally, the steady state period is denoted as a period when the motor rotates in one direction, except the period related to switching of the rotational direction.

Pattern b: The rate RT is subjected to variable control depending on the load torque applied to a motor.

The pattern b is effective in the case of avoiding the rotation speed of a motor from being decreased due to a load torque and causing the motor to rotate with keeping a set rotation speed.

Pattern c: In the case in which a plurality of rates for decreasing or increasing the voltage applied from the voltage application portion to a motor are set in advance, the rate RT is subjected to variable control depending on the rate selected out of the plurality of rates.

The pattern c meets such a request of changing the rate RT on the basis of intention of an operator, being a user. Pattern d: The rate RT is subjected to variable control depending on the distance from the apex of a treatment subject to a cutting tool.

The pattern c is required to suspend the treatment at the occasion in which the rate RT is varied so as to match the status of treatment progress. Conversely thereto, the pattern d has an advantage that the rate RT can be automatically changed so as to match the status of treatment progress.

According to the present invention, although heat generation of a motor can be suppressed due to the decrease of the load, measures for making the effect of the suppression of heat generation more prominent are provided. The measures are such that the control portion causes the back-and-forth time T of the motor specified by the following equation 2 to be subjected to variable control depending on the extent of heat generation of the motor.

$$T = Tcw + Tstop + Tccw \qquad \text{Equation 2}$$

Back-and-forth time T of a motor: Time required for forward rotation and reverse rotation of the motor
Tcw: Time required for forward rotation of the motor
Tccw: Time required for reverse rotation of the motor
Tstop: Standing time of the motor required when the rotational direction is switched from forward rotation to reverse rotation Advantageous Effects of Invention According to the present invention, a motor application voltage is decreased in advance of switching the polarity of motor application voltage at the rotational direction switching portion. When the polarity of motor application voltage is switched at the rotational direction switching portion thereafter, a low voltage is applied to the motor. The rotation speed of the motor immediately after switching of the rotational direction is thereby suppressed, and it can be prevented that a large rotation torque is applied to the cutting tool. As the result, it becomes possible to prevent giving a shock to the operator having a dental handpiece and the patient of treatment subject, and also becomes possible to reduce the load onto the motor and to suppress the heat generation.

BRIEF DESCRIPTION OF DRAWINGS

FIG. 4 is a diagram showing the flow of control in the control device according to a second embodiment.

DESCRIPTION OF EMBODIMENTS

First Embodiment

The present invention will be described below in detail on the basis of the embodiment shown in the attached drawings.

Figure 1:
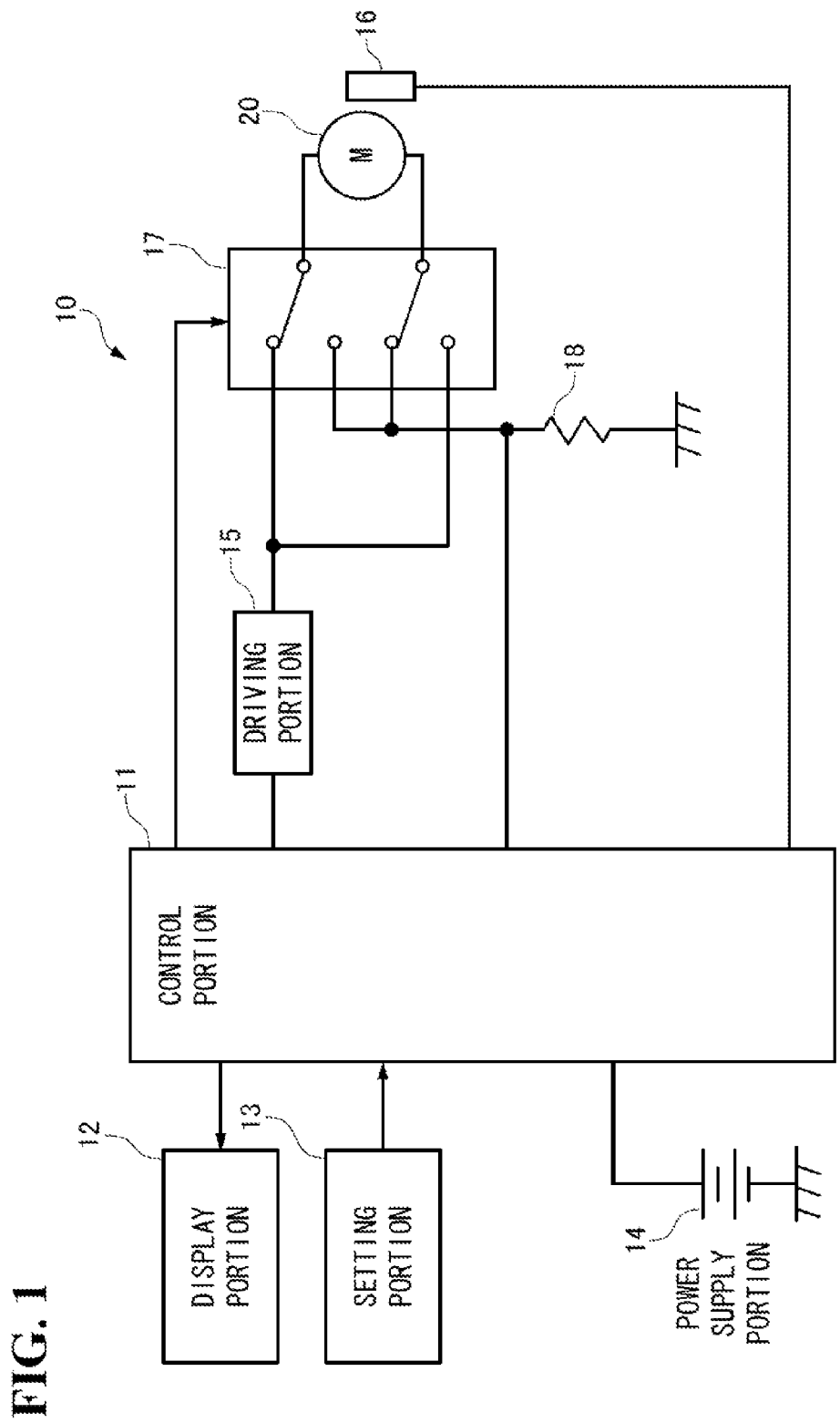
FIG. 1 is a diagram for explaining the configuration of a control device of a dental handpiece in the present embodiment (first embodiment).

As shown in FIG. 1, a control device 10 of a dental handpiece (hereinafter, simply called as handpiece) is one for controlling the operation of a motor 20 built in the handpiece, and the control device 10 comprises a control portion 11, a display portion 12, a setting portion 13, a power supply portion 14, a driving portion (voltage application portion) 15, a sensor 16, a relay (rotational direction switching portion) 17, and a current detection resistor 18.

The control portion 11 denotes a computer unit provided with a CPU, a memory, and the like.

The display portion 12 denotes a monitor, which displays information indicating rotation speeds, arising torques, and the like as the operating state of a motor 20, information for carrying out the operation setting of the motor 20 at the control portion 11, and the like, an indicator lamp, and the like.

The setting portion 13 includes an actuating button, a touch panel, a switch, or the like for setting the rotation speed, torque, rotation angle and other operating conditions of the motor 20 with respect to the control portion 11.

The power supply portion 14 supplies electric power for causing the control device 10 and the motor 20 of the handpiece to function.

The driving portion 15 regulates the voltage value to be applied to the motor 20 on the basis of the instruction from the control portion 11.

The sensor 16 includes a Hall element or the like for detecting the rotation angle of the motor 20.

The relay 17 carries out switching the polarity of voltage applied to the motor 20.

The current detection resistor 18 is one for detecting the current passed through the relay 17, and transforms the current, which has flowed to the motor 20, (motor current) into a voltage to feed back to the control portion 11. Since the motor current and the load torque have a proportional relationship in a DC motor, the control portion 11 is able to detect the load torque by means of the fed back voltage value.

Although the type of the motor 20 is not a question, an explanation will be given below on the precondition that a brushless direct current motor is used.

Figure 2:
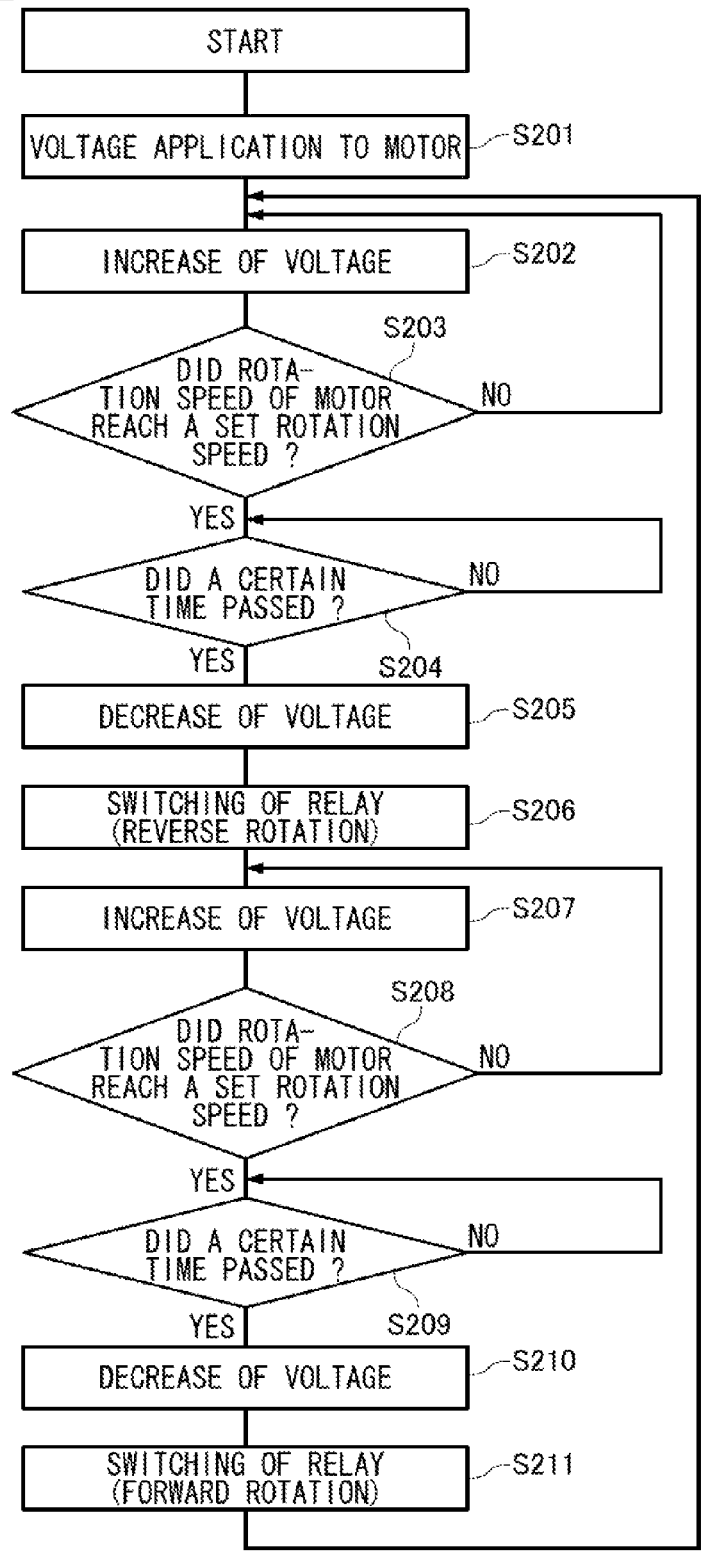
FIG. 2 is a diagram showing the flow of control in the control device according to the first embodiment.

Next, the details of the operation control for the motor 20 in the control device 10 of the handpiece as described above will be described using FIG. 2 and FIG. 3.

Upon actuation of the switch or the like for activating the handpiece, the control device 10 automatically implements control as described below on the basis of a computer program having been previously set.

In the first place, application of a voltage to the motor 20 is started according to an instruction from the control portion 11 (step S201).

Then, in the control portion 11, the voltage to be applied by the driving portion 15 at a previously determined step amount is obliquely increased (step S202). The motor 20 thereby increases the rotation speed at the rate corresponding to the applied voltage. This increasing rate of the rotation speed is called as an acceleration rate. This acceleration rate (the step amount at the occasion in which the applied voltage increases) is arbitrary in the present invention. That is, it is possible to control the motor 20 using a fixed value rate while being operated, or to perform variable control thereof during operation. Furthermore, it is also possible to calibrate the acceleration rate on the basis of the intention of the operator every time before a treatment using a handpiece is started. Specific examples of control and setting of the acceleration rate will be explained in a second embodiment and afterward.

Then, in the control portion 11, it is judged whether or not the rotation speed of the motor 20 reaches the set speed (step S203). To realize this, the rotation speed of the motor is detected at the sensor 16, and it is judged whether or not the detected value reaches the set value of rotation speed of the motor 20 (set speed), which is set by the setting portion 13 in advance.

As the result, in the case of not reaching the set speed, the process is returned to step S202 and the voltage to be applied to the motor 20 is increased until the rotation speed of the motor 20 reaches the set speed.

Figure 3:
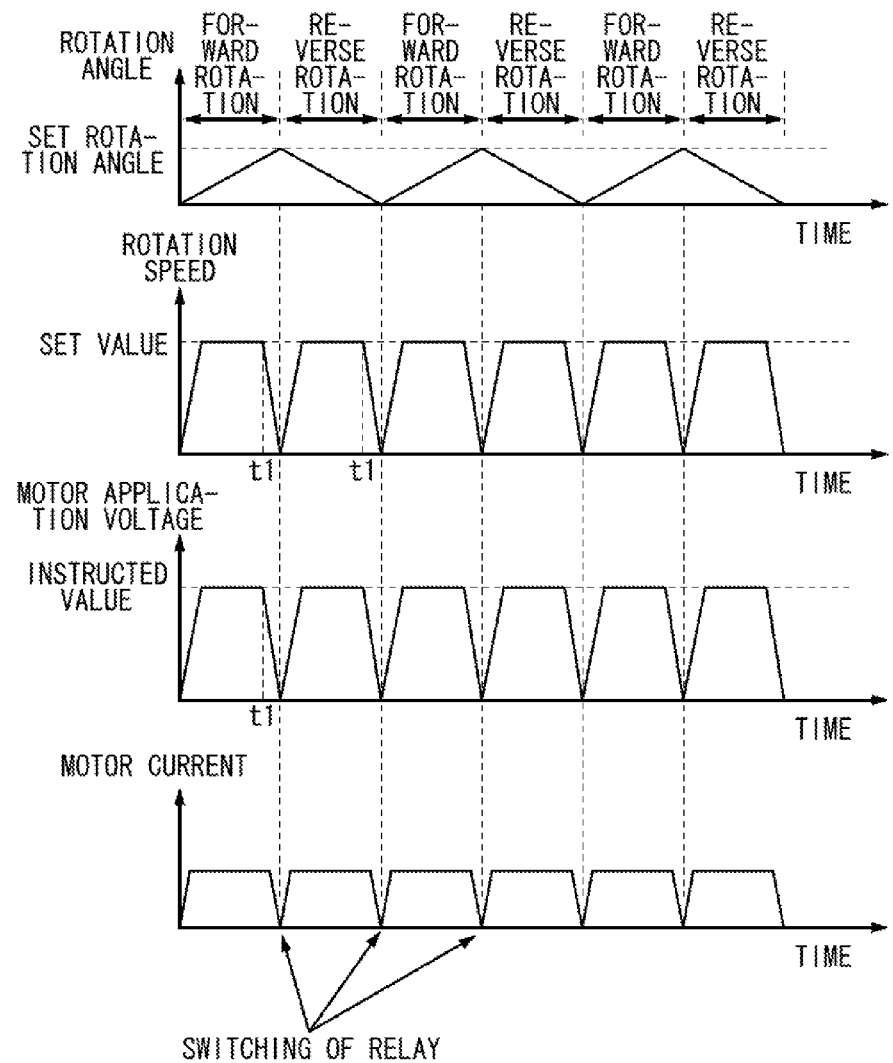
FIG. 3 is a chart showing variances of the rotation angle, rotation speed, motor application voltage, and motor current when the flow of control shown in FIG. 2 is implemented.

After the rotation speed of the motor 20 has reached the set speed, as shown in FIG. 3, the voltage to be applied to the motor 20 is obliquely decreased by a predetermined step amount at the point in time when having reached a predetermined certain time t1 (steps S204, S205). Then, the motor 20 is subjected to deceleration of the rotation speed at the rate corresponding to the applied voltage. This decreasing rate of the rotation speed is called as a deceleration rate. This deceleration rate (the step amount at the occasion in which the applied voltage decreases) is arbitrary in the present invention as with the above acceleration rate, in which it is possible to control the motor 20 using a fixed value while being operated, or the like. The voltage may be decreased until becoming 0V, or may be decreased to a predetermined voltage value.

After that, the relay 17 is switched, the polarity of the voltage to be applied to the motor 20 is switched, and the rotational direction of the motor 20 is switched to be reversely rotated (step S206).

Next, in the control portion 11, the voltage to be applied by the driving portion 15 at a previously determined step amount is obliquely increased as with the above steps S202 to S203 until the rotation speed of the motor 20 reaches the set speed (steps S207, S208).

After the rotation speed of the motor 20 has reached the set speed, the voltage to be applied to the motor 20 is obliquely decreased as with the above steps S202 to S203 at the point in time when having reached a predetermined certain time t1 from starting to rotate in the direction (steps S209, S210). The voltage may be decreased until becoming 0V, or may be decreased to a predetermined voltage value.

After that, the relay 17 is switched, the polarity of the voltage to be applied to the motor 20 is switched again, and the rotational direction of the motor 20 is switched to be forward rotated (step S211).

After that, the process is returned to step S202 and the above processes are automatically repeated until any actuation of stopping the operation of the handpiece is carried out by the switch or the like.

By proceeding like this, the handpiece performs a forward-reverse rotation movement in which the rotational direction of the motor 20 is reversed at every certain time, and the cutting tool repeats the forward rotation and reverse rotation at every certain time.

At this time, before switching the relay 17 and switching the rotational direction of the motor 20, i.e., in advance to switching the polarity of the voltage to be applied to the motor 20, the voltage to be applied to the motor 20 is decreased. It thereby becomes possible to prevent an inrush current from flowing into the motor 20 when the relay 17 is switched, and to prevent a large rotation torque from being applied to the cutting tool rotationally actuated by the motor 20. As the result, it becomes possible to prevent giving a shock to the operator having the dental handpiece and the patient of treatment subject. Moreover, the load onto the motor 20 can be reduced and heat generation of the motor 20 can be suppressed.

Incidentally, although the relay 17 is switched and the rotational direction of the motor 20 is reversed every time a certain time passes at steps S204, S209 in the above embodiment, it is not limited thereto, and a configuration may be adopted in which the relay 17 is switched and the rotational direction of the motor 20 is reversed every time the motor 20 rotates a predetermined angle. In this case, instead of steps S204, S209, the rotation angle of the motor 20 is detected by the sensor 16 and it is judged whether or not the rotation angle reaches a predetermined certain angle, and the process is shifted to steps S205, S210 at the point in time when having reached the certain angle.

Moreover, after the polarity of the voltage to be applied to the motor 20 is switched and the rotational direction of the motor 20 is switched so as to be reversed, the applied voltage is obliquely increased in the above embodiment. Although it is a preferable pattern of the present invention, it is also allowed to increase the applied voltage so as to vertically rise.

Incidentally, in the above embodiment, the configuration of a handpiece in itself is not limited at all.

Also as to the control device 10 of a handpiece, regarding the configuration in terms of hardware, details of the control by means of software, and the like, it is possible to choose any configuration from the above embodiment or to appropriately modify to other configurations without departing from the gist of the present invention.

Second Embodiment

It is possible, as described in the first embodiment, to render each of the acceleration rate and the deceleration rate to be a fixed value in the control device 10 of a handpiece. However, for example, motors 20 each have an individual difference, and the individual difference varies depending on the period of usage of the control device 10 or the motor 20. Accordingly, there is a fear that it becomes not possible to adequately enjoy the effects of the present invention of being able to prevent a large rotation torque from being applied to the cutting tool at the time of reverse actuation of switching from forward rotation to reverse rotation (or the converse thereof) when the acceleration rate and deceleration rate of a fixed value are used. On the other hand, if the acceleration rate and deceleration rate are lessened, it becomes possible to prevent a large rotation torque from being applied to the cutting tool; however, it means to reduce cutting efficiency. On this account, an example of calibration for setting a preferable acceleration rate and deceleration rate will be explained with reference to FIG. 4, FIGS. 5A to 5C in the second embodiment.

Figure 5A:
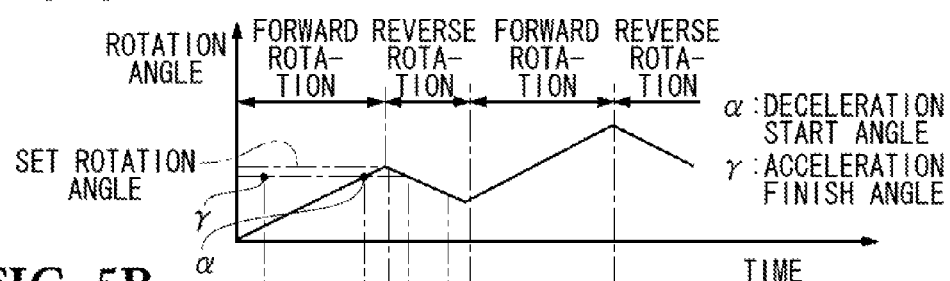
FIGS. 5A, 5B, 5C are charts showing variances of the rotation angle, rotation speed, motor current, respectively, when the flow of control shown in FIG. 4 is implemented.
Figure 5B:
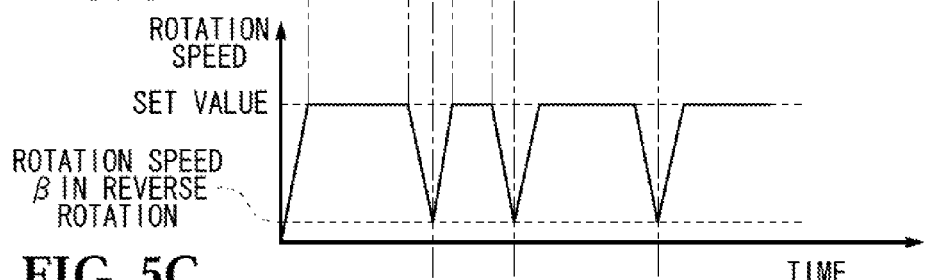
Figure 5C:
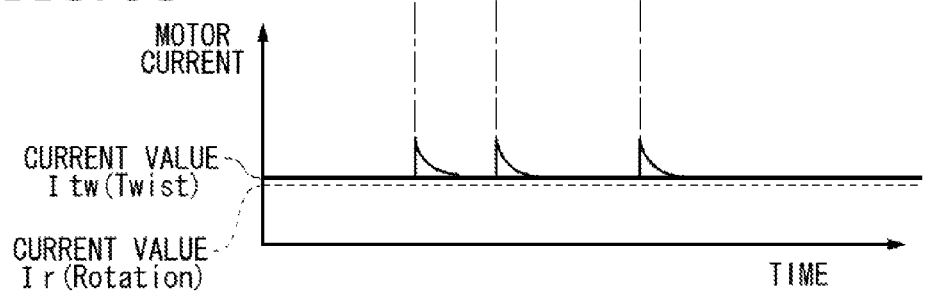

In the state of no load in which the motor 20 is rotated in one direction, the current value is constant as the current value Ir (Rotation) of FIG. 5C indicates; while, when the motor 20 is reverse-rotated, an inrush current arises as the current value Itw (Twist) of FIG. 5C indicates. The second embodiment proposes to set a preferable acceleration rate or deceleration rate, which is able to avoid outstanding reduction of cutting efficiency while reducing the inrush current, on the basis of the relationship between the current value Ir and the current value Itw.

Here, the acceleration rate or deceleration rate is derived from the acceleration finish angle γ, deceleration start angle α, rotation speed β in reversal rotation, and set rotation speed, which are indicated in FIGS. 5A, 5B. Accordingly, the current value Itw is varied by adjusting the acceleration finish angle γ and the other parameters, and calibration of the control device 10 is carried out. The procedure of this calibration is done on the basis of an instruction of the control portion 11.

The procedure of this calibration is shown in FIG. 4. First, the motor 20 is rotated so as to reach the set rotation speed (step S301 in FIG. 4). The motor current (current value Ir) at this time is fed back to the control portion 11 through the current detection resistor 18 and is stored in the control portion 11 (step S302 in FIG. 4). The stored current value Ir is rendered to be a criterion for setting the acceleration rate or deceleration rate, which is the object of this calibration. Incidentally, the rotation of the motor 20 called here denotes a rotation only in one direction of either forward rotation or reverse rotation.

Next, the control portion 11 applies a voltage to the motor 20 so as to reach the set rotation speed after reversing thereof from forward rotation to reverse rotation (step S303 in FIG. 4). The control portion 11 conducts initial setting of each of the acceleration finish angle γ, deceleration start angle α, and rotation speed β in reversal rotation, and causes forward-reverse rotation of the motor 20 to be performed on the basis of the initial setting. The motor current (current value Itw) at the time of being reversed is also fed back to the control portion 11 through the current detection resistor 18 and is stored in the control portion 11 (step S304 in FIG. 4).

Subsequently, the control portion 11 judges whether or not the stored current value Ir and current value Itw satisfy the following equation 1 (step S305 in FIG. 4).

$$Itw \leq Ir \cdot K \qquad \text{Equation 1}$$

K of the equation 1 is a constant that is set in the control portion 11 and is set in order to limit the current value Itw within a predetermined range, taking the current value Ir as the criterion. Although a value exceeding 1 is normally given to K, there is a tendency that the closer K is to 1, the less the inrush current can be suppressed, but the cutting efficiency decreases. Conversely, there is a tendency that the further K is from 1, the larger the inrush current becomes, but the cutting efficiency increases. In the control portion 11, K can also be varied.

If the control portion 11 judges so that the stored current value Ir and current value Itw satisfy the equation 1, the set rotation speed, acceleration finish angle γ, deceleration start angle α and rotation speed β in reversal rotation having been initially set are stored in the control portion 11, and the calibration is completed (step S305 (Yes), step S309 in FIG. 4).

If the control portion 11 judges so that the stored current value Ir and current value Itw do not satisfy the equation 1, the control portion 11 resets each of the deceleration start angle α, rotation speed β in reversal rotation and acceleration finish angle γ having been initially set (step S305 (No), step S306, step S307, step S308 in FIG. 4).

After that, the control portion 11 conducts implementation of reverse actuation of the motor 20 (step S303 in FIG. 4), storing of the current value Itw (step S304 in FIG. 4), and judgment whether or not the stored current value Ir and current value Itw satisfy the equation 1 (step S305 in FIG. 4) as with before. If judged to be Yes at the step S305, the control portion 11 stores the reset acceleration finish angle γ, deceleration start angle α and rotation speed β in reversal rotation, and completes the calibration (step S309 in FIG. 4). On the other hand, if judged that the stored current value Ir and current value Itw still do not satisfy the equation 1 (when judged to be No at the step S305), the control portion 11 repeats resetting of each of the deceleration start angle α, rotation speed β in reversal rotation and acceleration finish angle γ (step S306, step S307, step S308), storing of the current value Itw (step S304 in FIG. 4), and judgment whether or not the stored current value Ir and current value Itw satisfy the equation 1 (step S305 in FIG. 4) until the current value Ir and current value Itw satisfy the equation 1.

As described above, by performing the calibration according to the second embodiment, since the acceleration rate and deceleration rate suitable to each of the motors 20 can be set even though the motors 20 each have an individual difference, it is possible to restrain the reduction of cutting efficiency at a minimum, while preventing to give a shock to the operator and the patient of treatment subject.

Moreover, according to the second embodiment, it is possible to effectively suppress an inrush current. Furthermore, it is also possible to enhance the accuracy of torque control by using the current value Itw for the torque control of the motor 20 at the time of forward-reverse rotation.

Third Embodiment

The control portion 11 can perform variable control of one of or both the acceleration rate and deceleration rate. An example of performing variable control of the acceleration rate and deceleration rate will be described in a third embodiment.

Figure 6A:
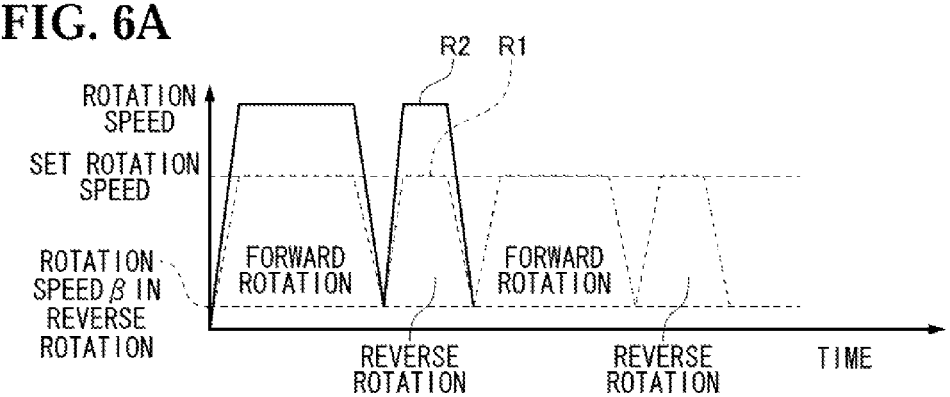
FIGS. 6A, 6B are charts showing variances of the rotation speed, motor application voltage, respectively, when the control according to a third embodiment is implemented.
Figure 6B:
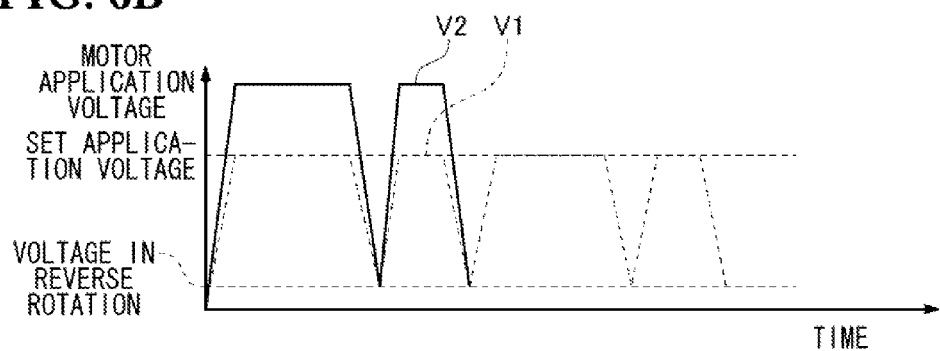
Figure 7A:
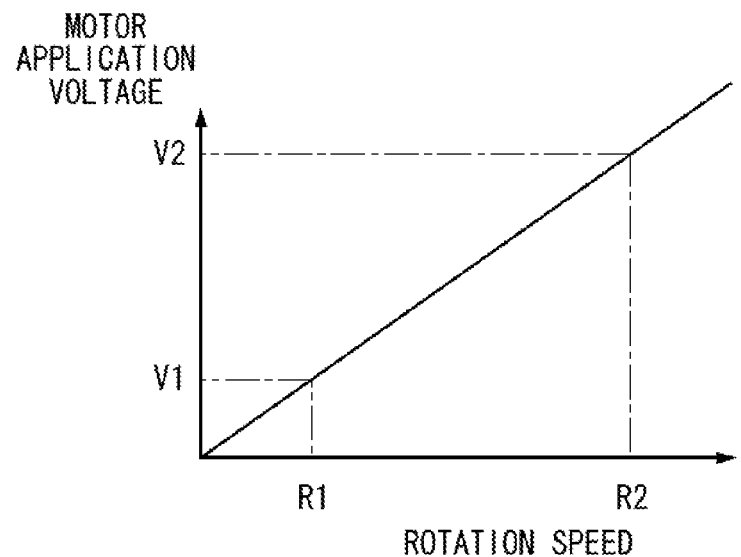
FIG. 7A shows the relationship between the rotation speed and motor application voltage when the control according to the third embodiment is implemented.

In FIGS. 6A, 6B, there is shown one example thereof, which is on the precondition that the set rotation speed of the motor 20 is variably controlled between R1 and R2, and the set application voltage is subjected to variable control in between V1 and V2 according to this set rotation speed. In the control portion 11 in this case, the relationship between the rotation speed and the application voltage of the motor 20 is stored. As shown in FIG. 7A, for example, it is assumed that the rotation speeds R1, R2 and the motor application voltages V1, V2 are in a proportional relationship (motor application voltage V=a×rotation speed R, a: proportionality constant). Incidentally, this relational expression is taken by causing the motor 20 to rotate in one direction without a load.

Figure 8:
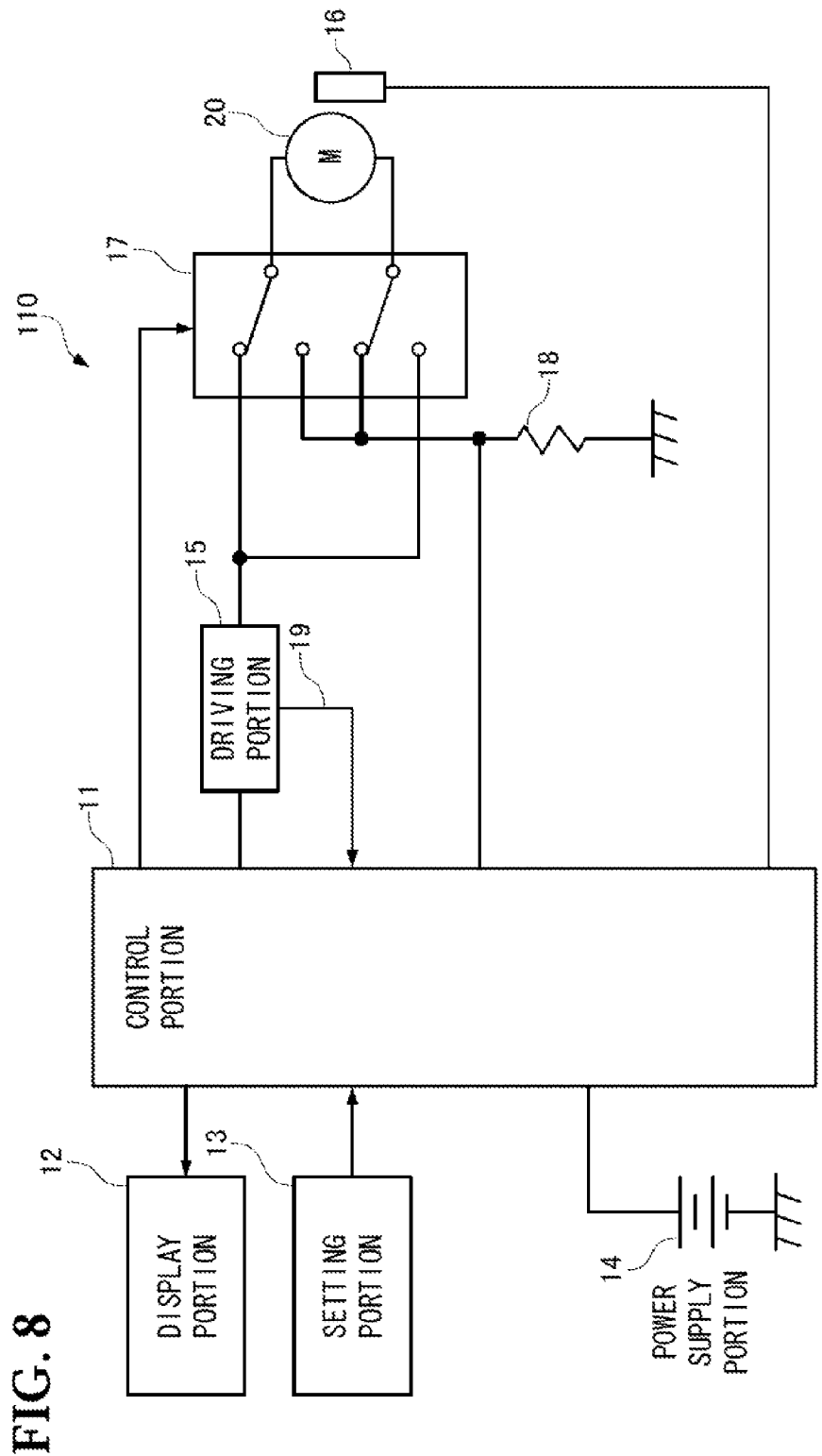
FIG. 8 is a diagram for explaining the configuration of the control device for implementing the control according to the third embodiment.

The control portion 11 controls the motor application voltage on the basis of the above relational expression and, at that occasion, appropriately sets a time during when the rotation speed of the motor 20 reaches the set rotation speed according to the set rotation speed (=set voltage). For example, a time required for one cycle (rotation angle) from starting of forward rotation to turning to reverse rotation (or the converse thereof) is denoted as Tx, and the require time (rotation angle) for enabling to bring the rotation speed of the motor 20 to the set rotation speed is denoted as Tr; then, the ratio of Tr occupying Tx is set to be constant. By doing so, in response to causing the set rotation speed of the motor 20 to be subjected to variable control, the acceleration rate and deceleration rate of the motor 20 are also subjected to variable control. This control is performed by that the control portion 11 of a control device 110 detects the application voltage to the motor 20 through a voltage detection line 19 as shown in FIG. 8.

Figure 7B:
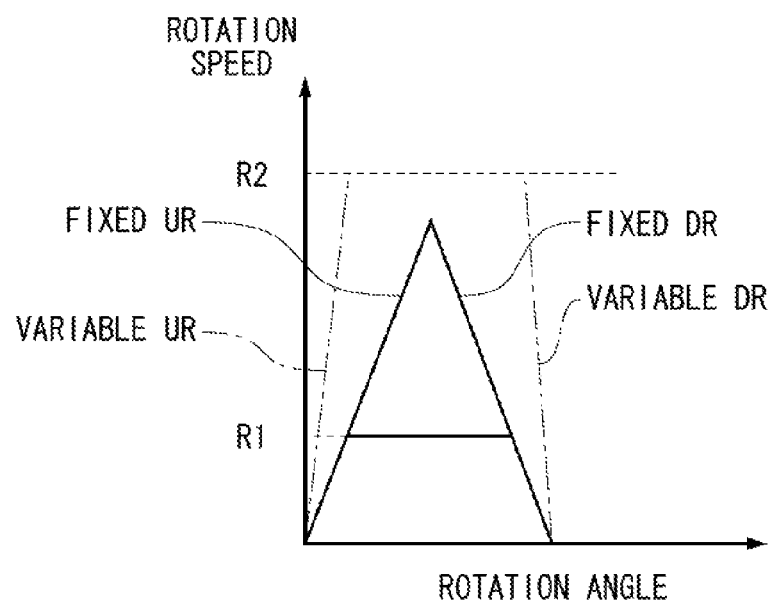
FIG. 7B shows the relationship between the rotation speed and rotation angle when an acceleration rate and deceleration rate are fixed.

Then, when the acceleration rate (UR) and deceleration rate (DR) are each rendered to be a fixed rate and the set rotation speed of the motor 20 is varied (the set rotation speed is variable), it happens that the rotation speed does not reach the set rotation speed R2 as shown in FIG. 7B. In contrast, it becomes possible to bring the rotation speed to reach the set rotation speed R2 by performing variable control of the acceleration rate (UR) and deceleration rate (UR) even if the set rotation speed is changed to R2. Incidentally, although the case in which the set rotation speed is variable has been mentioned here, the same holds true also as to the case of performing variable control of the angle of forward rotation (or reverse rotation) required for one cycle, i.e., the set rotation angle.

By the way, in the case in which the number of sensors for detecting the rotation speed of the motor 20, i.e., in the case in which the resolution for detection signals of the rotation speed of the motor 20 is low, it is difficult to render the time Tr (angle) required for reaching the set rotation speed to be constant only with speed feedback from the detection signals of the sensors. However, according to the embodiment described above, since the speed feedback is not used, it is possible to perform variable control of the acceleration rate and deceleration rate even if the resolution for detection signals of the rotation speed is low. However, the present invention does not limit the pattern for performing variable control of the acceleration rate and deceleration rate to ones described above.

Although the control patterns described above are based on the premise that any load is not applied to the motor 20, it includes not only the case of not cutting a tooth (teeth) at all but also the case of performing cutting of a minute amount. On the other hand, when a load is applied to the motor 20 and a torque (load torque) acts thereon, variable control of the acceleration rate and deceleration rate in accordance with the load torque can be performed as described below.

Figure 9A:
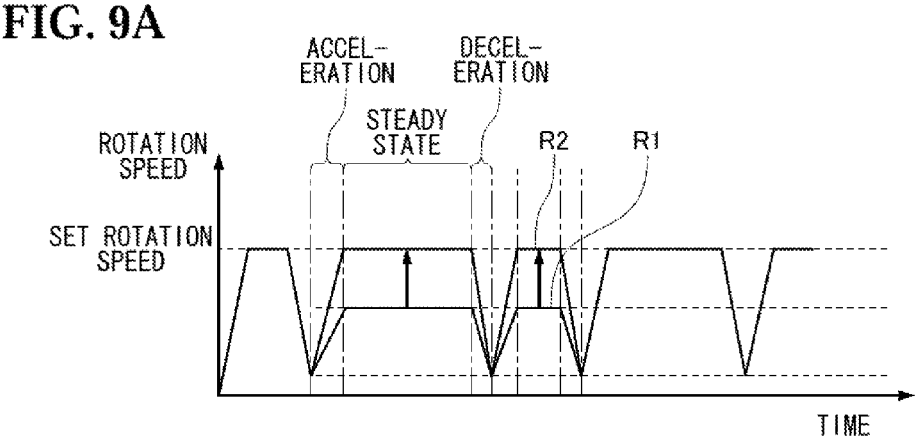
FIGS. 9A, 9B, 9C are charts showing variances of the rotation speed, motor application voltage, load torque, respectively, when the other control according to the third embodiment is implemented.
Figure 9B:
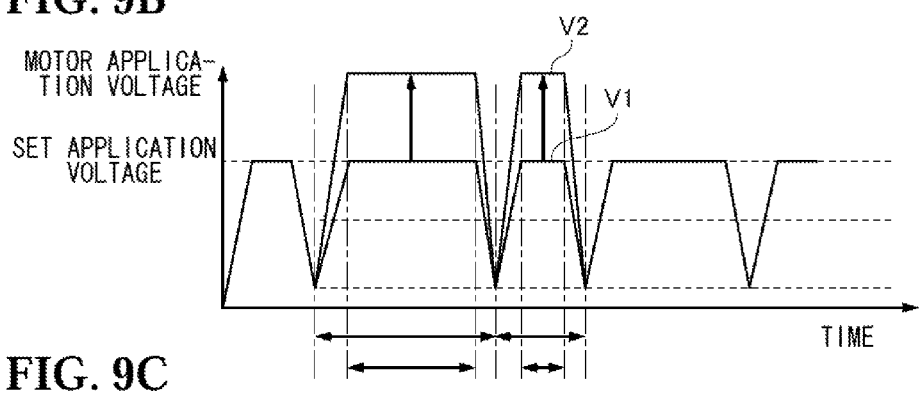
Figure 9C:
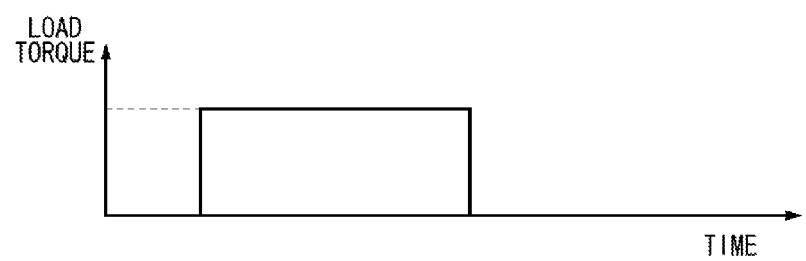

When a load torque is applied to the motor 20 during operating as shown in FIG. 9C, if the set motor application voltage (V1) is as it is, the rotation speed of the motor 20 is rendered to be R1 lower than the set rotation speed R2, and the cutting efficiency is reduced. The control portion 11 carries out a correction of raising the set motor application voltage from V1 to V2 when a load torque is applied to the motor 20, as shown in FIG. 9B. In response to this correction of the motor application voltage, the rotation speed of the motor 20 is corrected so as to reach the set rotation speed R2, as shown in FIG. 9A.

In order to carry out the above correction, the control portion 11 stores load torques applied to the motor 20 and the motor application voltages to be corrected when the load torques are applied so as to correspond with each other. The control portion 11 detects the torque applied to the motor 20, determines the correction value of the set application voltage in accordance with the detected torque, and controls the motor 20 through use of the determined voltage value. Incidentally, the control portion 11 can detect the load torque applied to the motor 20 on the basis of the voltage value fed back from the current detection resistor 18.

Here, by setting the time until reaching the set rotation speed at the time of acceleration and deceleration of the motor 20 similarly as with the case of the motor 20 without a load described above, the acceleration rate and deceleration rate are subjected to variable control. At steady rotation provided between acceleration and deceleration, the control portion 11 keeps the motor application voltage at the set motor application voltage, by which it is realized that the motor 20 is rendered to be the rotation speed R2 similar as with the time of no load.

As explained above, according to the present embodiment, since the rotation speed of the motor 20 can be controlled to be constant by varying the acceleration rate and deceleration rate in accordance with the load torque of the motor 20, the cutting efficiency is not decreased even if the load torque varies.

Fourth Embodiment

There is a case in which an acceleration rate and deceleration rate are desired to be varied due to the intention of an operator. For example, in the case in which a medical treatment is applied to a shallow portion of a root canal, an acceleration rate, deceleration rate laying emphasis on cutting efficiency are adopted, and in the case in which a medical treatment is applied to a deep portion near the work length (the distance from a reference point to an apical constriction at the occasion of forming a root canal), an acceleration rate, deceleration rate laying emphasis on softening a shock are adopted. Accordingly, in a fourth embodiment, an example responding to the needs of operators like this will be described with reference to FIGS. 10A to 10C.

Figure 10A:
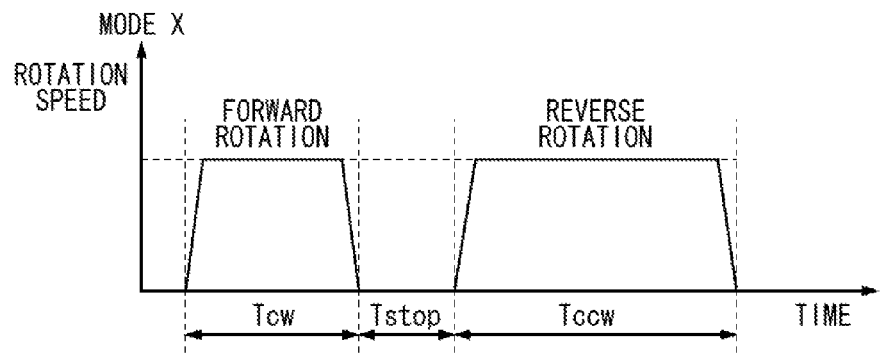
FIGS. 10A, 10B, 10C show variances of the rotation speed at mode X, mode Y, mode Z, respectively, when the control according to a fourth embodiment is implemented.
Figure 10B:
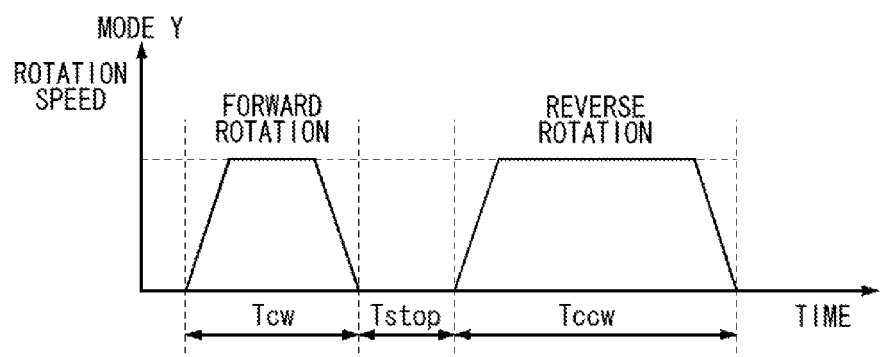
Figure 10C:
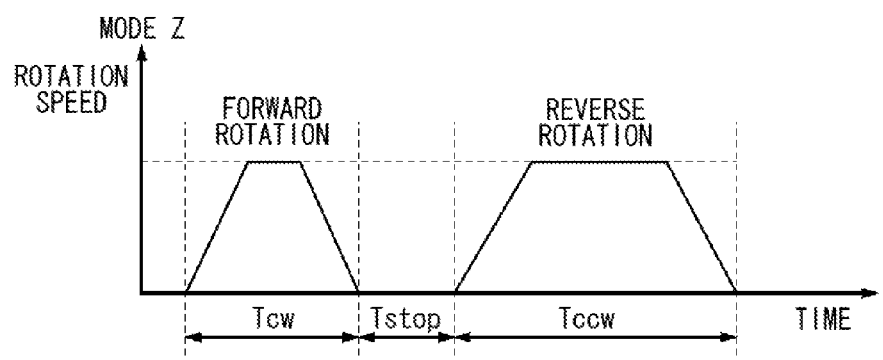

The fourth embodiment allows an operator to select the acceleration rate, deceleration rate from three steps (levels) of mode X (FIG. 10A), mode Y (FIG. 10B) and mode Z (FIG. 10C). The mode X, mode Y and mode Z are set in the control portion 11 in accordance with following criteria. And, for example, the mode X, mode Y and mode Z are displayed on the display portion 12 so that any one thereof can be selected in the setting portion 13. From the setting portion 13, the operator selects a mode responding to the medical treatment. The control portion 11 controls the operation of the motor 20 on the basis of any one of the mode X, mode Y and mode Z selected at the setting portion 13.

Mode X: Medical treatment of a shallow portion of a root canal

Mode Y: Mid-section between mode X and mode Z

Mode Z: Medical treatment of a deep portion of a root canal near the work length The mode X, mode Y and mode Z can be set specifically as follows.

When one cycle (time) of forward rotation including acceleration, deceleration is denoted as Tcw, ratios (%) of times spent for acceleration, deceleration in this Tcw are determined. The smaller this ratio is, the steeper the acceleration, deceleration become and the cutting efficiency can be enhanced, and the larger this ratio is, the milder the acceleration, deceleration become and a shock can be softened. For example, it is possible to set the value at 10% as to the mode X, at 20% as to the mode Y and at 30% as to the mode Z. It is also possible to display this value "10%" or the like on the display portion 12 so that the operator can select it in the setting portion 13. Also in regard to reverse rotation, it is possible to set the mode X, mode Y and mode Z similarly as with forward rotation.

As with the above description, according to the fourth embodiment, since any user of the control device 10 including an operator can set the acceleration rate, deceleration rate by selecting from a plurality of them, which are set in advance, based on his/her intention, it is possible to apply a favorable medical treatment depending on the area of medical treatment or the conditions of the patient.

Moreover, even at an area as with a deep portion of a root canal where has hitherto been cut by a cutting tool rotated by hand, cutting can be done by use of the dental handpiece.

Although the acceleration rate, deceleration rate are rendered to be 3 steps (mode X, Y, Z) in FIGS. 10A to 10C, the present invention is not limited thereto, the acceleration rate, deceleration rate may be set in 2 steps, or 4 steps or further more steps. In addition, although the acceleration rate, deceleration rate of the respective steps are rendered to be fixed values in the fourth embodiment, the present invention includes that an user sets the acceleration rate, deceleration rate at his/her choice. For example, it is possible to steplessly adjust the acceleration rate, deceleration rate by providing a dial for adjusting the acceleration rate, deceleration rate in the setting portion 13.

Moreover, although the mode X, mode Y and mode Z are used for both forward rotation and reverse rotation in the above, different modes may also be provided for each of the forward rotation and reverse rotation.

Furthermore, in the above, one cycle of forward rotation (Tcw), one cycle of reverse rotation (Tccw) for each of the mode X, mode Y and mode Z are rendered to be constant, one cycle of forward rotation, however, one cycle of reverse rotation may be varied as to each of the mode X, mode Y and mode Z. In the above, although the standing time of the motor 20 between forward rotation and reverse rotation (Tstop) for the mode X, mode Y and mode Z is rendered to coincide to each other, the standing time (Tstop) for each of the mode X, mode Y and mode Z may be varied.

Fifth Embodiment

The fourth embodiment provides an arrangement in which an user sets an acceleration rate, deceleration rate; in this case, however, the treatment is to be suspended at the occasion in which the acceleration rate, deceleration rate are varied to match the status of treatment progress. Accordingly, in a fifth embodiment, an example is presented that is able to automatically vary the acceleration rate, deceleration rate so as to match the status of treatment progress.

Figure 12:
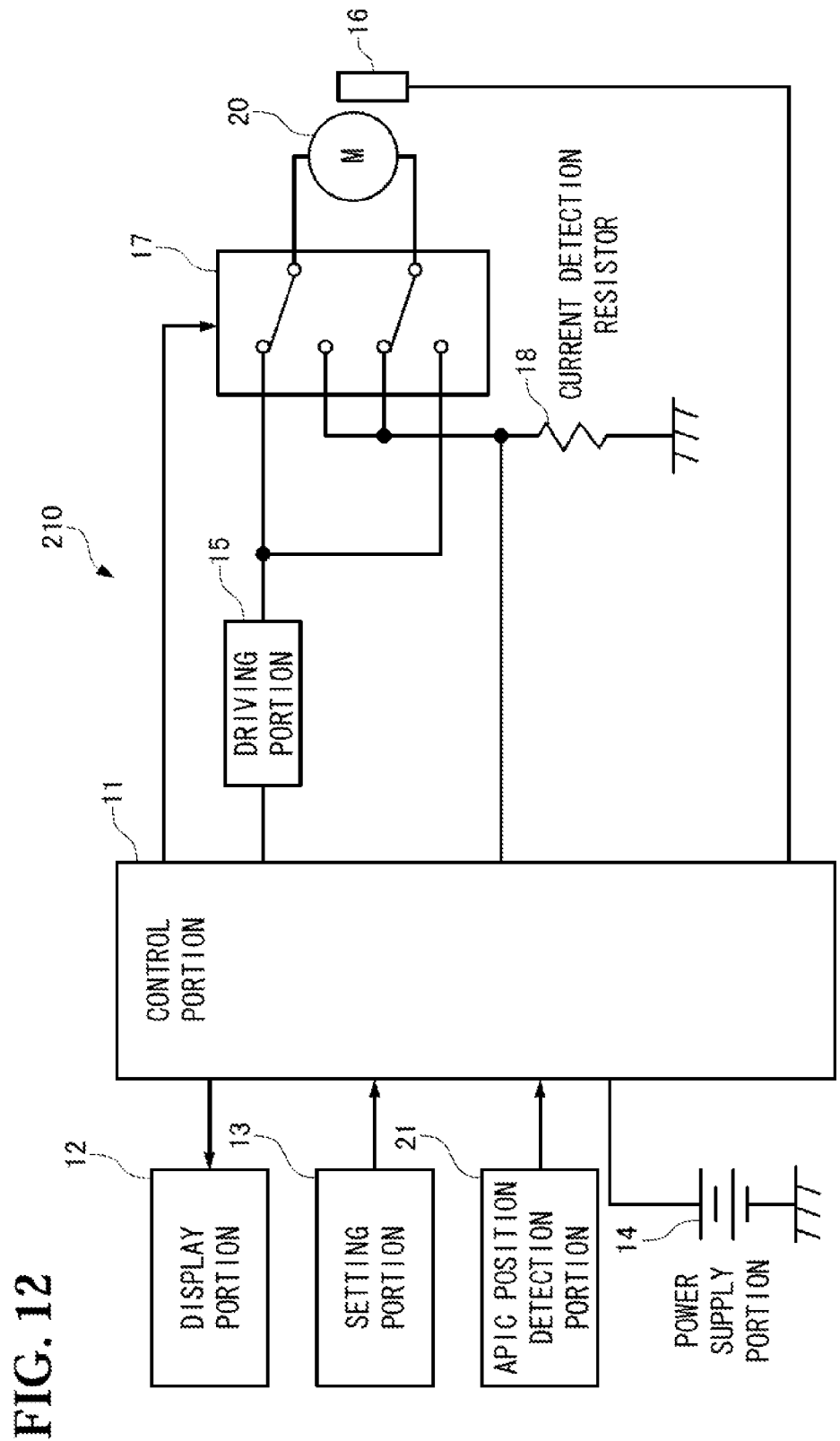
FIG. 12 is a diagram for explaining the configuration of a control device according to the fifth embodiment.

A control device 210 according to the fifth embodiment includes an apex position detection portion 21 as shown in FIG. 12. Incidentally, the control device 210 includes the same components as those of the control device 10 of the first embodiment except provided with the apex position detection portion 21.

In the fifth embodiment, the control device 210 includes the apex position detection portion 21 and a handpiece, the motor 20 of which is controlled by the control device 210, also has a root canal length measurement function. The handpiece having this function measures the distance from an apex to the cutting tool by detecting the apex position while applying the root canal treatment. That is, while allowing the cutting tool to have the function as a measurement electrode, this cutting tool is inserted into the tooth canal of a tooth, and an electrical measuring signal is applied in between the measurement electrode and an oral cavity electrode, which is separately provided, to detect the apex. Incidentally, as the method for detecting an apex, there are known a method for detecting the apex by applying a measuring signal in between the measurement electrode and the oral cavity electrode and by detecting the resistance value between both electrodes; a method for detecting the apex by applying a plurality of measuring signals having different frequencies with each other and by using ratios of impedances in the root canal obtained in response to the respective measuring signals, and the like, the present invention allows anyone of these detection methods to be adopted. The apex position detection portion 21 gives the measured distance L between the apex and the cutting tool to the control portion 11.

Figure 11:
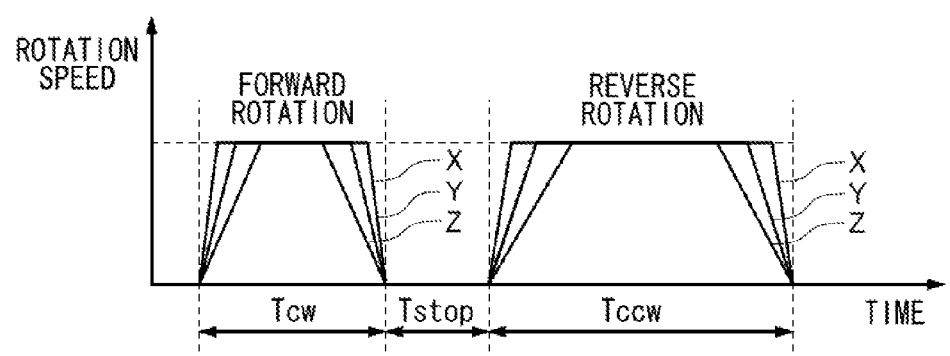
FIG. 11 shows variances of the rotation speed when the control according to a fifth embodiment is implemented.

The control portion 11 stores the acceleration rate, deceleration rate so as to correspond to the distance L from the apex to the cutting tool in advance. For example, 3 modes of mode X, mode Y and mode Z are prepared similarly as with the fourth embodiment as shown in FIG. 11, and the correspondence thereof is enabled as follows. Incidentally, $L_0$, $L_1$, $L_2$, $L_3$ have a relationship of $L_0 < L_1 < L_2 < L_3$, and $L_3$ corresponds with a work length (root canal length).

Mode X: $L_2$ to $L_3$ (a shallow portion of a root canal)

Mode Y: $L_1$ to $L_2$ (mid-section between mode X and mode Z)

Mode Z: $L_0$ to $L_1$ (near an apex)

And, the acceleration rate, deceleration rate are set at the value of 10% as to the mode X, the value of 20% as to the mode Y and the value of 30% as to the mode Z similarly with the fourth embodiment. By doing so, the control device 210 actuates the motor 20 with an acceleration rate, deceleration rate laying emphasis on cutting efficiency at a shallow portion of a root canal, and actuates the motor 20 with an acceleration rate, deceleration rate laying emphasis on softening a shock due to reverse rotation when the cutting tool comes close to the apex. Like this, since the control device 210 automatically varies the acceleration rate, deceleration rate depending on the position of the cutting tool, it is not necessary for the operator to suspend the treatment on the way thereof for varying the acceleration rate, deceleration rate, which thereby results in that an efficient treatment can be carried out.

It is possible to set the acceleration rate, deceleration rate besides the 3 steps also in the fifth embodiment. In addition, it is also possible to set the acceleration rate, deceleration rate in proportion to the distance L from an apex to a cutting tool in advance, or to cause the acceleration rate, deceleration rate to be subjected to stepless variable control by preparing a relationship equation between the distance L and the acceleration rate, deceleration rate and by calculating the acceleration rate, deceleration rate on the basis of the obtained distance L. In addition thereto, it is needless to say that setting of different modes to forward rotation and reverse rotation, and the like pointed out in the fourth embodiment can also be adopted to the fifth embodiment.

Sixth Embodiment

According to the first embodiment to the fifth embodiment in the above, as the result that it is possible to prevent a large rotation torque from being applied to a cutting tool, a load onto the motor 20 is reduced and heat generation thereof can be suppressed. In a sixth embodiment presented below, the effect of this suppression of heat generation can be made more remarkable.

A time (back-and-forth time) T required for one cycle during which the motor 20 performs forward rotation and reverse rotation can be derived from the sum of a time Tcw required for forward rotation (one cycle), a standing time Tstop of the motor 20 required for switching the rotational direction, and a time Tccw required for reverse rotation (one cycle) as indicated with the following equation 2.

$$T=Tcw+Tstop+Tccw \qquad \text{Equation 2}$$

Figure 13A:
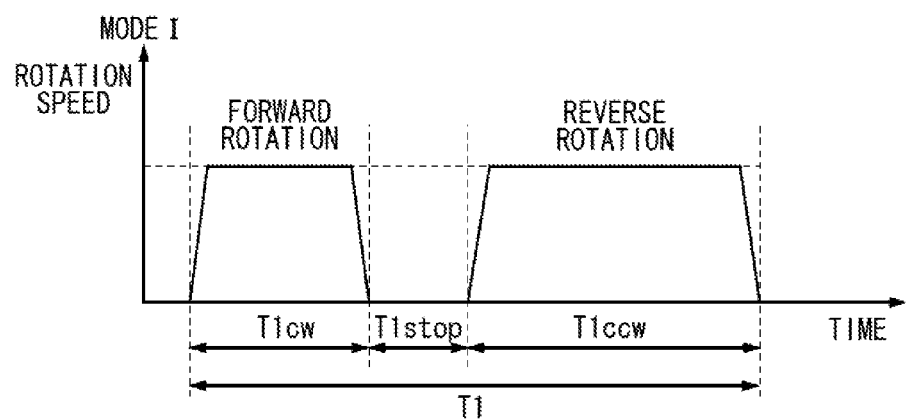
FIGS. 13A and 13B show variances of the rotation speed when the control according to a sixth embodiment is implemented.
Figure 13B:
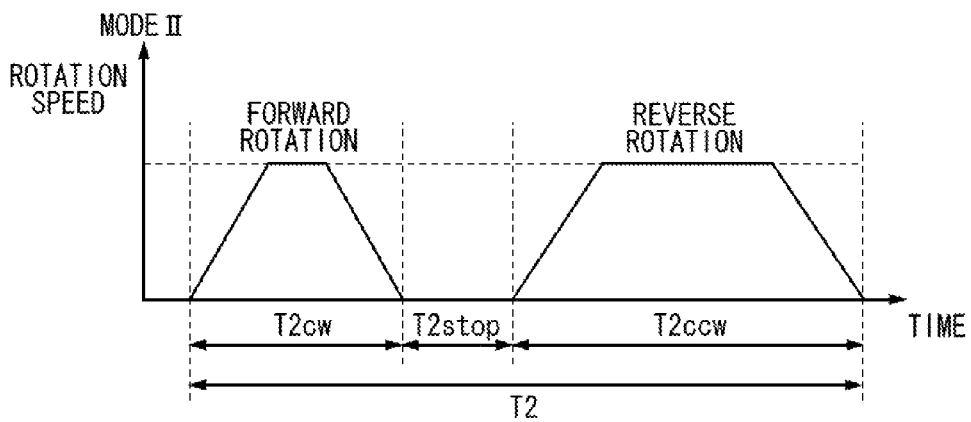
Figure 14:
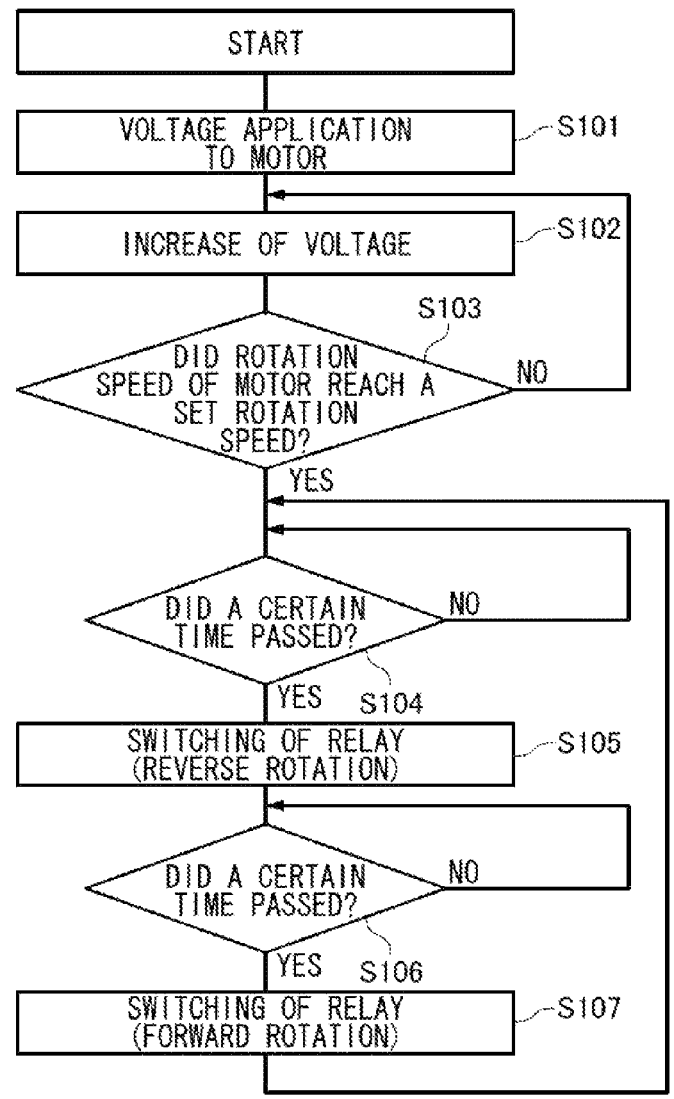
FIG. 14 is a diagram showing a flow of conventional control.
Figure 15:
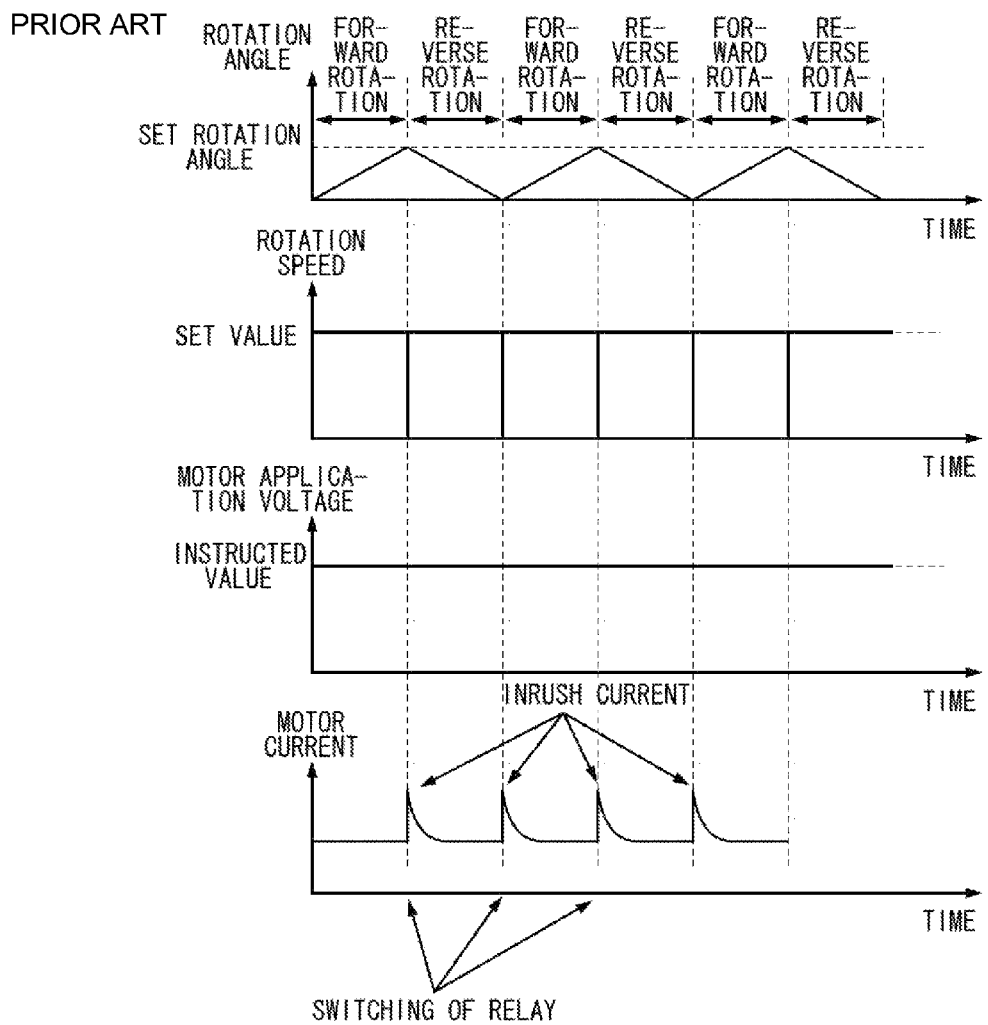
FIG. 15 is a chart showing variances of the rotation angle, rotation speed, motor application voltage, and motor current when the flow of control shown in FIG. 14 is implemented.

The reciprocal of the back-and-forth time T is the back-and-forth times (or frequency) f (f=1/T), and the larger the back-and-forth times f of the motor 20 become, the more the heat generation amount of the motor 20 becomes larger. Accordingly, in the sixth embodiment, the extent of heat generation of the motor 20 is pursued, and the back-and-forth times f is to be limited in accordance with the extent. That is, the back-and-forth time T1 is rendered to be the sum of the forward rotation time T1cw, the standing time T1stop of the motor 20, and the reverse rotation time T1ccw until the extent of heat generation reaches a threshold th, as shown in FIG. 13A. When the extent of heat generation exceeds the threshold th, the back-and-forth time T2 (>T1) is rendered to be the sum of the forward rotation time T2cw, the standing time T2stop of the motor 20, and the reverse rotation time T2ccw as shown in FIG. 13B. Like this, the heat generation of the motor 20 is suppressed by causing the back-and-forth time T to be longer, i.e., by limiting the back-and-forth times f to be less. At this occasion, by suppressing the acceleration rate, deceleration rate, T1cw<T2cw, T1ccw<T2ccw can be realized, and the back-and-forth times f can also be made small while keeping the rotation angle at the time of reverse rotation.

$$T1=T1cw+T1stop+T1ccw \qquad \text{(mode I)}$$

$$T2=T2cw+T2stop+T2ccw \qquad \text{(mode II)}$$

$$T1<T2, T1cw<T2cw, T1stop<T2stop, T1ccw<T2ccw$$

For that reason, the control portion 11 possesses forward rotation times T1cw, T2cw, standing times T1stop, T2stop of the motor 20, reverse rotation times T1ccw, T2ccw as control parameters. In addition, the control portion 11 acquires the extent of heat generation of the motor 20.

This extent of heat generation can be acquired through various means. As a rather direct means, a temperature sensor having, for example, a thermistor is provided in the vicinity of the motor 20 of a handpiece, and the measured temperature can be used as the extent of heat generation. When the measured temperature of the handpiece is equal to or less than a threshold th, the control portion 11 controls the motor 20 with the mode I (T1), while when the temperature of the handpiece exceeds the threshold th, the control portion 11 controls the motor 20 with the mode II (T2). While controlling the motor 20 with the mode II (T2) after the temperature of the handpiece has exceeded the threshold th, if the temperature of the handpiece decreases to become equal to or less than the threshold th, the control portion 11 controls the motor 20 with the mode I (T1). By doing so, abnormal heat generation of the motor 20 can be prevented.

In the above, although an example of increasing all of the T1cw, T1stop, T1ccw has been presented, the present invention is not limited thereto, but allows any one of the T1cw, T1stop, T1ccw to be increased.

The physical quantity used for judging the extent of heat generation of the motor 20 is not limited to temperature. For example, it is possible to specify the extent of heat generation using electric power supplied to the motor 20. This technique is such that electric power supplied to the motor 20 is sequentially detected, and the detected values are integrated for obtaining the integral value. And, an arrangement can be provided in which when this integral value is equal to or less than a threshold, the control portion 11 controls the motor 20 with the mode I (T1), while when this integral value exceeds the threshold, the control portion 11 controls the motor 20 with the mode II (T2). This integral value is obtained by integrating electric power with time, and can therefore be approximately regarded as a criterion that indicates heat generation of the motor 20.

Incidentally, it is possible to choose any configuration from the above embodiments or to modify the configurations of the embodiments without departing from the gist of the present invention.

REFERENCE SIGNS LIST

10, 110, 210 Control device
11 Control portion
12 Display portion
13 Setting portion
14 Power supply portion
15 Driving portion (Voltage application portion)
16 Sensor
17 Relay (Rotational direction switching portion)
18 Current detection resistor
19 Voltage detection line
20 Motor
21 Apex position detection portion

The invention claimed is:

1. A control device of a dental handpiece, comprising:
a voltage application portion for applying voltage to a motor for rotating a cutting tool mounted to the dental handpiece, the motor being built in the dental handpiece;
a rotational direction switching portion for switching a rotational direction of the motor by switching a polarity of voltage, which is applied to the motor by the voltage application portion; and
a control portion for controlling a magnitude of the voltage applied by the voltage application portion,
wherein the control portion obliquely decreases voltage in advance of switching of voltage polarity, which is conducted by the rotational direction switching portion, the voltage being applied to the motor by the voltage application portion.

2. The control device of a dental handpiece according to claim 1, wherein voltage to be applied to the motor from the voltage application portion is obliquely increased after the voltage polarity has been switched.

3. The control device of a dental handpiece according to claim 1, wherein the control portion controls so that the rotational direction switching portion carries out switching of the voltage polarity at every lapse of a predetermined certain time.

4. The control device of a dental handpiece according to claim 1, further comprising a sensor for detecting a rotation angle of the motor,
  wherein the control portion controls so that, when a rotation angle of the motor detected by the sensor reaches a predetermined certain angle, the rotational direction switching portion carries out switching of the voltage polarity.

5. The control device of a dental handpiece according to claim 2, wherein the control portion has a function of calibrating a rate RT, which increases or decreases voltage to be applied to the motor from the voltage application portion.

6. The control device of a dental handpiece according to claim 5, wherein the control portion performs variable control of the rate RT.

7. The control device of a dental handpiece according to claim 6, wherein the control portion performs variable control of the rate RT depending on a rotation speed of the motor.

8. The control device of a dental handpiece according to claim 6, wherein the control portion performs variable control of the rate RT depending on a load torque applied to the motor.

9. The control device of a dental handpiece according to claim 6, wherein a plurality of rates causing voltage to decrease or increase, the voltage being applied to the motor from the voltage application portion, and the control portion performs variable control of the rate RT depending on a rate selected out of the plurality of rates.

10. The control device of a dental handpiece according to claim 6, wherein the control portion performs variable control of the rate RT depending on a distance from an apex of a treatment subject to the cutting tool.

11. The control device of a dental handpiece according to claim 1, wherein the control portion performs variable control of a back-and-forth time T of the motor depending on an extent of heat generation of the motor, the back-and-forth time T being specified by $$T = Tcw + Tstop + Tccw$$

where the back-and-forth time T of the motor is a time required for forward rotation and reverse rotation of the motor;
  Tcw is a time required for forward rotation of the motor;
  Tccw is a time required for reverse rotation of the motor; and
  Tstop is a standing time of the motor required when the rotational direction is switched from forward rotation to reverse rotation.

12. A control device of a dental handpiece, comprising:
  a voltage application portion for applying voltage to a motor for rotating a cutting tool mounted to the dental handpiece, the motor being built in the dental handpiece;
  a rotational direction switching portion for switching a rotational direction of the motor by switching a polarity of voltage, which is applied to the motor by the voltage application portion; and
  a control portion for controlling a magnitude of the voltage applied by the voltage application portion,
  wherein the control portion obliquely decreases voltage in advance of switching of voltage polarity, which is conducted by the rotational direction switching portion, the voltage being applied to the motor by the voltage application portion,
  wherein voltage to be applied to the motor from the voltage application portion is obliquely increased after the voltage polarity has been switched, and
  wherein the control portion controls so that the rotational direction switching portion carries out switching of the voltage polarity at every lapse of a predetermined certain time.

13. A control device of a dental handpiece, comprising:
  a voltage application portion for applying voltage to a motor for rotating a cutting tool mounted to the dental handpiece, the motor being built in the dental handpiece;
  a rotational direction switching portion for switching a rotational direction of the motor by switching a polarity of voltage, which is applied to the motor by the voltage application portion;
  a control portion for controlling a magnitude of the voltage applied by the voltage application portion; and
  a sensor for detecting a rotation angle of the motor,
  wherein the control portion obliquely decreases voltage in advance of switching of voltage polarity, which is conducted by the rotational direction switching portion, the voltage being applied to the motor by the voltage application portion,
  wherein voltage to be applied to the motor from the voltage application portion is obliquely increased after the voltage polarity has been switched, and
  wherein the control portion controls so that, when a rotation angle of the motor detected by the sensor reaches a predetermined certain angle, the rotational direction switching portion carries out switching of the voltage polarity.

\* \* \* \* \*

UNITED STATES PATENT AND TRADEMARK OFFICE
CERTIFICATE OF CORRECTION

| | | |
|---|---|---|
| PATENT NO. | : 9,186,226 B2 | Page 1 of 1 |
| APPLICATION NO. | : 14/119993 | |
| DATED | : November 17, 2015 | |
| INVENTOR(S) | : Makoto Kunisada | |

It is certified that error appears in the above-identified patent and that said Letters Patent is hereby corrected as shown below:

Specification

Column 3, line 15 should read --The pattern c is required to suspend the treatment at the--.

Signed and Sealed this
Fifteenth Day of March, 2016

Michelle K. Lee
*Director of the United States Patent and Trademark Office*